United States Patent [19]
Breitenbach et al.

[11] Patent Number: 6,150,424
[45] Date of Patent: Nov. 21, 2000

[54] SOLID FOAMED ACTIVE SUBSTANCE PREPARATIONS

[75] Inventors: Jörg Breitenbach, Mannheim; Horst Baumgartl, Mainz, both of Germany

[73] Assignee: BASF Aktiengesellschaft, Ludwigshafen, Germany

[21] Appl. No.: 09/254,012

[22] PCT Filed: Aug. 21, 1997

[86] PCT No.: PCT/EP97/04550

§ 371 Date: Mar. 1, 1999

§ 102(e) Date: Mar. 1, 1999

[87] PCT Pub. No.: WO98/09616

PCT Pub. Date: Mar. 12, 1998

[30] Foreign Application Priority Data

Sep. 3, 1996 [DE] Germany ............ 196 35 676

[51] Int. Cl.$^7$ .................................. A61K 47/32
[52] U.S. Cl. ...................... 514/772.5; 514/772.5
[58] Field of Search .................. 424/465; 514/772.4

[56] References Cited

U.S. PATENT DOCUMENTS

| 4,801,460 | 1/1989 | Goertz et al. | 424/465 |
| 4,880,585 | 11/1989 | Klimesch et al. | 264/141 |
| 5,369,131 | 11/1994 | Poli et al. | 514/772.4 |

FOREIGN PATENT DOCUMENTS

| 240 906 | 10/1987 | European Pat. Off. . |
| 240 904 | 10/1989 | European Pat. Off. . |
| 694 376 | 1/1996 | European Pat. Off. . |

*Primary Examiner*—S. Mark Clardy
*Assistant Examiner*—Konata M. George
*Attorney, Agent, or Firm*—Keil & Weinkauf

[57] ABSTRACT

Solid foamed active ingredient preparations based on melt-processable polymers, obtainable by extrusion of a melt of one or more polymers which comprises active ingredient and which is impregnated with a volatile, physiologically acceptable blowing agent and expanded.

9 Claims, No Drawings

SOLID FOAMED ACTIVE SUBSTANCE PREPARATIONS

DESCRIPTION

The present invention relates to solid, partially or completely foamed active ingredient forms based on melt-processable polymers.

The invention furthermore relates to processes for producing active ingredient forms of this type.

It is generally known that foamed plastics can be produced by extruding melts comprising volatile blowing agents.

It is furthermore known, for example from EP-A 240 904, to prepare solid drug forms by extruding active ingredient-containing polymer melts with subsequent shaping.

Rapid-release drug forms are, as a rule, obtained by using insoluble but swellable disintegrants to bring about rapid disintegration of the drug form.

Rapid release can also be obtained with drug forms produced by melt extrusion by using relatively low molecular weight, water-soluble thermoplastic polymers as matrix polymers. However, the disadvantage of this is that on use of such polymers there are frequently problems with the storage stability of the finished drug forms.

It is an object of the present invention to find active ingredient-containing preparations which can be obtained by the economically attractive melt-extrusion process and permit controlled release of the active ingredient.

We have found that this object is achieved by the active ingredient forms defined at the outset. We have also found processes for producing such active ingredient forms.

The solid, foamed active ingredient preparations according to the invention may contain as active ingredients all the substances which can be incorporated without decomposition into the polymer melt under the processing conditions.

Examples of suitable active ingredients are:

acebutolol, acetylcysteine acetylsalicylic acid, aciclovir, alprazolam, albumin, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, azemetacin [sic], beclometasone [sic], benscerazide [sic], benzalkonium hydroxide, benzocaine, benzoic acid, betametasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazolin, cefixime, cefotaxime, ceftazidine, ceftriaxone, cefuroxime, chloramphenicol, chlorhexidine, chlorpheniramine, chlortalidone, choline, ciclosporin, cilastatin, cimetidine, ciprofloxacin, cisapride, cisplatin, clarithromycin, clavulanic acid, clomibramine [sic], clonazepam, clonidine, clotrimazole, clozapine, codeine, colestyramine, cromoglicic [sic] acid, cyanocobalamin, cyproterone, desogestrel, dexamethasone, dexpanthenol, dexthromethorphan [sic], dextropropoxiphene, diazepam, diclofenac, digoxin, dihydrocodeine, dihydroergotamine, dilthiazem [sic], diphenhydramine, dipyridamole, dipyrone, disopyramide, domperidone, dopamine, doxocycline [sic], enalapril, enrofloxacin, ephedrine, epinephrine, ergocalciferol, ergotamine, erythromycin, estradiol, ethinylestradiol, etoposide, Eucalyptus Globulus [sic], famotidine, felodipine, fenofibrate, fenoterol, fentanyl, flavin mononucleotide, fluconazole, flunarizine, fluorouracil, fluoxetine, flurbiprofen, flutamide, furosemide, gemfibrozil, gentamicin, Ginkgo Biloba [sic], glibenclamine [sic], glipizide, Glycyrrhiza Glabra [sic], guaifenesin, haloperidol, heparin, hyaluronic acid, hydrochlorothiazide, hydrocodone, hydrocortisone, hydromorphone, hydroxytetracycline, ipratropium hydroxide, ibuprofen, imipenem, indomethacin, iohexol, iopamidol, isosorbide dinitrate, isosorbide mononitrate, isotredinoin [sic], ketotifen [sic], ketoconazole, ketoprofen, ketorolac, labetalon [sic], lactulose, lecithin, levocarnitine, levodopa, levoglutamide, levonorgestrel, levothyroxine, lidocaine, lipase, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misobrostol [sic], morphine, multivitamins and minerals, nystatin, N-methylephedrine, naftidrofuril [sic], naproxen, neomycin, nicardipine, nicergoline, nicotinamide, nicotine, nicotinic acid, nifedipine, nimodipine, nitrendipine, nizatidine, norethisterone, norfloxacin, norgestrel, nortriphthyline [sic], ofloxacin, omeprazole, ondansetron, pancreatin, panthenol, pantoprazole, pantothenic acid, paracetamol, penicillin G, penicillin V, phenobarbital, phenoxifylline [sic], phenylephrine, phenylpropanolamine, phenytoim [sic], piroxicam, polymyxin B, povidone-iodine, pravastatin, prazepam, prazosin, prednisolone, prednisone, proglumetacin, propafenone, propranolol, pseudoephedrine, pyridoxine, quinidine, ramipril, ranitidine, reserpine, retinol, riboflavin, rifampicin, rutoside, saccharin, salbutamol, salcatonin, salicyl [sic] acid, simvastatin, somatropin [sic], sotalol, spironolactone, sucralfate, sulbactam, sulfamethoxazole, sulpiride, tamoxifen, tegafur, tenoxicam, teprenone, terazosin, terbutaline, terfenadine, theophylline, thiamine, thiaprofenic [sic] acid, ticlopidine, timolol, tranexamic acid, tretinoin, triamcinolone acetonide, triamterene, trimethoprim, troxerutin, uracil, valproic acid, vancomycin, verapamil, vitamin E, volinic [sic] acid, zidovudine, zotepine.

Vitamins can also be formulated according to the invention. These include vitamins of the A group, of the B group, meaning, besides B1, B2, B6 and B12 and nicotinic acid and nicotinamide, also compounds with vitamin B properties such as adenine, choline, pantothenic acid, biotin, adenylic acid, folic acid, orotic acid, pangamic acid, carnitine, p-aminobenzoic acid, myo-ionsitol [sic] and a-lipoic acid. Furthermore vitamins of the C group, D group, E group, F group, H group, I and J groups, K group and P group.

Very particularly preferred active ingredients according to the invention are ibuprofen, acetylsalicylic acid, paracetamol, phenazone, flurbiprofen, captopril, nifedipine, acetylcysteine, naftidrofuryl, verapamil and furosemide.

Also suitable as active ingredients are crop protection agents, other biocides or veterinary medicinal substances.

Suitable melt-processable polymers for the polymer matrix are according to the invention amorphous thermoplastic polymers.

Particularly suitable polymers are water-soluble, melt-processable homo- or copolymers of N-vinylpyrrolidone or mixtures of such polymers. The polymers normally have glass transition temperatures in the range from 80 to 190, preferably 90 to 170, ° C. Examples of suitable homopolymers are polymers with Fikentscher K values in the range from 10 to 30. Suitable copolymers may contain as comonomers unsaturated carboxylic acids, eg. methacrylic acid, crotonic acid, maleic acid, itaconic acid, and their esters with alcohols having 1 to 12, preferably 1 to 8, carbon atoms, furthermore hydroxyethyl or hydroxypropyl acrylate and methacrylate, (meth)acrylamide, the anhydrides and monoesters of maleic acid and itaconic acid (with the monoester preferably being formed only after the polymerization), or vinyl monomers such as N-vinylcaprolactam, vinyl acetate, vinyl butyrate and vinyl propionate, or else mixtures of said comonomers. Thus, suitable examples are terpolymers of N-vinylpyrrolidone, vinyl acetate and vinyl propionate.

Preferred comonomers are acrylic acid and, particularly preferably, vinyl acetate. The comonomers can be present in amounts of from 20 to 70% by weight. Very particularly preferred copolymers according to the invention are those obtained from 60% by weight of N-vinylpyrrolidone and 40% by weight of vinyl acetate.

Examples of suitable polymers are also homo- or copolymers of vinyl chloride, polyvinyl alcohols, polystyrene, poly . . . rates, polyhydroxybutyrates or copolymers of ethylene and vinyl acetate.

The active ingredient preparations may furthermore also comprise starches, degraded starches, casein, pectin, chitin, chitosan, gelatin or shellac as matrix components which can be processed with the addition of conventional plasticizers in the melt.

It is furthermore possible for the preparations according to the invention to comprise conventional pharmaceutical ancillary substances such as bulking agents, lubricants, mold release agents, flow regulators, plasticizers, dyes and stabilizers in amounts of up to about 50% by weight. These amounts and those stated hereinafter are in each case based on the total weight of the preparation (=100%).

Examples of bulking agents which may be mentioned are the oxides of magnesium, aluminum, silicon and titanium, and lactose, mannitol, sorbitol, xylitol, pentaerythritol and its derivatives, the amount of bulking agent being about 0.02–50, preferably 0.2–20, % by weight.

Examples of flow regulators which may be mentioned are the mono-, di- and triglycerides of long-chain fatty acids such as $C_{12}$, $C_{14}$, $C_{16}$ and $C_{18}$ fatty acid, waxes such as carnauba wax, and the lecithins, the amount being about 0.1–30, preferably 0.1–5, % by weight.

Examples of plasticizers which may be mentioned are, besides low molecular weight polyalkylene oxides such as polyethylene glycol, polypropylene glycol and polyethylene/propylene glycol, also polyhydric alcohols such as propylene glycol, glycerol, pentaerythritol and sorbitol, and sodium diethyl sulfosuccinate, glycerol mono-, di- and triacetate and polyethylene glycol stearic ester. The amount of plasticizer is moreover about 0.5–15, preferably 0.5–5, % by weight.

Examples of lubricants which may be mentioned are stearates of aluminum or calcium, and talc and silicones, the amount thereof being about 0.1–5, preferably 0.1–3, % by weight.

Examples of stabilizers which may be mentioned are light stabilizers, antioxidants, radical scavengers and stabilizers against microbial attack, the amount thereof preferably being about 0.01–0.05% by weight.

In order to produce the preparations according to the invention, the active ingredient component can be either previously mixed with the polymer and subsequently extruded or else metered during the extrusion into the polymer melt comprising blowing agent.

The ratios of the amounts of the individual component [sic] in the preparation can be varied within wide limits. The amount of active ingredient can be from 0.1 to 90% of the weight of the active ingredient preparation, depending on the effective dose and rate of release of the active ingredient. The amount of the polymer can be from 10 to 99.9% by weight. In addition, from 0 to 50% by weight of one or more ancillary substances can be present. Completely foamed active ingredient preparations according to the invention are preferably produced by extrusion of a melt which, besides one or more active ingredients, comprises one or more melt-processable polymers and, where appropriate, conventional ancillary substances, the melt being impregnated with volatile, physiologically acceptable blowing agents.

Suitable volatile, physiologically acceptable blowing agents are gaseous blowing agents such as carbon dioxide, nitrogen, air, inert gases such as helium or argon, chlorofluorocarbons or dinitrogen oxide (laughing gas), with carbon dioxide and/or nitrogen being preferred.

The melt is preferably produced in the extruder, particularly preferably in a twin screw extruder. The mixing of the active ingredient(s) with the polymers and, where appropriate, other additives can take place before or after the polymers are melted by processes customary in industry. It is advisable, especially with temperature-sensitive active ingredients, to add these only after the thermoplastic has melted. The melt can be obtained at temperatures from 50 to 200, preferably 100 to 180, °C., the suitable temperature depending in particular on the glass transition temperature of the polymer(s). The polymers will normally be melted at temperatures above their glass transition temperature.

The melt is impregnated with the blowing agent preferably under pressures of from 10 to 300 bar, particularly preferably 50 to 200 bar. Under these conditions, from 1 to 15% by weight of blowing agent dissolves in the melt.

The impregnation with plasticizing blowing agents such as $CO_2$ lowers the viscosity of the melt so that extrusion of the melt which comprises blowing agent can take place at lower temperatures than with a corresponding melt without blowing agent. This property of the polymer melt comprising blowing agent is beneficial for the incorporation of thermally labile active ingredients.

The melt comprising blowing agent is preferably cooled to temperatures in the range from 0 to 50° C. above the glass transition temperature of the polymer, or mixture of polymers, without blowing agent.

It is advisable for particularly temperature-sensitive active ingredients to be added to the melt after the addition of the blowing agent and reduction in temperature.

The process according to the invention can be carried out in a single extruder with different temperature zones. However, a tandem extrusion system consisting of two extruders coupled together is preferred, with the first extruder in which the melting of the polymer and the charging of the melt with blowing agent takes place preferably being a twin screw extruder with an efficient mixing action, and the second extruder being a single screw extruder with little shear effect and high cooling efficiency.

The still plastic extrudate emerging from the die expands under the atmospheric pressure prevailing outside the extruder to a foam.

The degree of foaming of the active ingredient preparation can be controlled by the amount of blowing agent added and the extrusion temperature. A high degree of foaming results in a lower density and thus a high rate of dissolution of the active ingredient form. If higher densities are required, a high blowing agent content which is beneficial for the preparation can be reduced, by degassing in the direct vicinity of the die gap, to such an extent that an only slightly foamed product is obtained. The foamed active ingredient preparation is subsequently shaped to the required active ingredient forms in each case, for example by pelleting, granulating or tableting by known processes.

The solid, completely foamed active ingredient preparations normally have densities in the range from 200 to 1000 g/l, preferably 200 to 800 g/l.

Another embodiment of the process according to the invention relates to the production of multilayer partially or completely foamed forms comprising active ingredients by coextrusion. This entails at least two compositions, each of which comprises at least one of said thermoplastic binders, and at least one of which comprises an active ingredient and at least one of which is impregnated in the manner previously described with a gaseous physiologically acceptable blowing agent, being coextruded and subsequently shaped to or [sic] required dosage form.

Before the coextrusion, the composition for each layer of the active ingredient form is prepared separately. For this purpose, the relevant starting components are processed in a separate extruder, under the conditions described for the previous variant of the process, to melts comprising active ingredients. It is possible in this case to operate under conditions which are optimal for the specific materials in each layer. It is possible, for example, to select a different processing temperature for each layer. Each of the compositions can, for example, also be impregnated with different amounts of blowing agent so that layers which differ in the degree of foaming are produced.

The molten or plastic compositions from the individual extruders are introduced into a coextrusion die and extruded. The shape of the coextrusion dies depends on the required active ingredient form. For example, dies with a flat gap, called slit dies, and annular dies are suitable. The design of the die depends on the polymeric binder which is used and on the required shape.

Extrusion from the coextrusion die is followed by shaping to the required active ingredient form or drug form. It is possible in this connection to produce a large number of shapes depending on the coextrusion die and mode of shaping. For example, open multilayer tablets can be produced from an extrudate from a slit die, which has, in particular, two or three layers, by punching out or cutting out, eg. with an incandescent wire. Alternatively, open multilayer tablets can be separated through an annular die by a hot-cut process, ie. by cutting or chopping the extrudate immediately after emerging from the die, or preferably by a cold-cut process, ie. by cutting or chopping the extrudate after at least partial cooling.

Closed active ingredient forms, ie. forms in which the layer comprising active ingredient is completely enveloped by a layer without active ingredient, are obtained in particular through an annular die by treating the extrudate in a suitable nip device. It is advantageous in this case if, after the outer layer has cooled, the inner layer of the multilayer tablet is still capable of plastic deformation on entry into the nip device. It is possible in this way to produce, in particular, tablets, preferably oblong tablets, coated tablets, pastilles and pellets.

In another variant of the process, foamed forms comprising active ingredients can be produced by extruding a melt which, besides one or more active ingredients, comprises at least one thermoplastic binder, subjecting the still plastic melt to a shaping, and then impregnating the solid form comprising active ingredient under pressure with one of the abovementioned gaseous blowing agents, for example in a conventional autoclave under pressures in the range from 10 to 300 bar, preferably 50 to 200 bar, and subsequently expanding on decompression to atmospheric pressure, the impregnated form expands to a partially or completely foamed form.

The degree of foaming depends on the duration of the impregnation process and can be set as required. This variant of the process is preferably suitable for producing partially foamed forms which have an outer foamed shell and an unfoamed core and thus display a stepped release profile.

The foamed forms can also be provided with a conventional coating which is permeable to active ingredient, so that floating forms can be obtained in a straightforward manner. Such floating forms can be used for pharmaceutical purposes or else for veterinary medicinal or agricultural engineering products, for example for producing slowly sinking fish feed. The solid, foamed active ingredient preparations obtained according to the invention, which comprise the active ingredient homogeneously dispersed in the polymeric matrix, dissolve very rapidly and thus permit rapid release of the active ingredient. The foamed active ingredient preparations can be obtained in a straightforward and economic manner by the process according to the invention. It is also advantageous that, owing to the viscosity-reducing effect of the blowing agent, extrusion is possible at distinctly lower temperatures than without blowing agent, so that the active ingredients are exposed to less thermal stress.

EXAMPLE 1

A mixture of 20% by weight of ibuprofen and 80% by weight of a polymer of 60% by weight of N-vinylpyrrolidone and 40% by weight of vinyl acetate with a K value of 30 was melted in a twin screw extruder at 150° C. and impregnated with carbon dioxide under a pressure of 100 bar inside the extruder, so that 4% by weight of carbon dioxide were dissolved in the melt. The melt loaded with blowing agent was cooled to 80° C. and extruded in a flanged single screw extruder. Emergence of the extrudate into atmospheric pressure while simultaneously cooling to room temperature resulted in a solid foamed active ingredient preparation. On visual inspection under a microscope, the foams comprising active ingredients showed a rate of dissolution in water which was 30 times higher than for a corresponding compact active ingredient form obtained by extrusion in the absence of the blowing agent.

EXAMPLE 2

A mixture of 26% by weight of ibuprofen and 74% by weight of a copolymer of 60% by weight of N-vinylpyrrolidone and 40% by weight of vinyl acetate with a K value of 30 was melted at 150° C. and extruded in a twin screw extruder. The still thermoplastic extrudate was shaped by the process described in EPA 240 906 into oblong tablets with a weight of 650 mg, which were subsequently impregnated under a carbon dioxide pressure of 100 bar in an autoclave at 40° C. for four hours, subsequently decompressed and cooled to room temperature. The rate of release was determined using a USP XII [sic] paddle apparatus. After 30 min, 85% of the active ingredient was released. By comparison with this, after 30 min only 40% of the active ingredient was released from oblong tablets produced in a similar way but not impregnated and foamed.

We claim:

1. A solid, shaped and partially or completely foamed active ingredient form comprising at least one thermoplastic polymer.

2. An active ingredient form as claimed in claim 1, comprising as thermoplastic polymer a homo- or copolymer of N-vinylpyrrolidone.

3. An active ingredient form as claimed in claim 1, comprising an active ingredient selected from ibuprofen, ketoprofen, flurbiprofen, acetylsalicylic acid, verapamil, paracetamol, nifedipine, caffeine, captopril and vitamins or mixtures of two or more of these active ingredients.

4. A process for producing active ingredient forms as claimed in claim 1, which comprises extruding a melt comprising, besides one or more active ingredients, at least one thermoplastic polymer and a volatile, physiologically acceptable blowing agent, and shaping the expanded extrudate to the required active ingredient form.

5. A process for producing active ingredient forms as claimed in claim 1, which comprises coextruding at least two melts, each of which comprises a thermoplastic polymer and at least one of which comprises one or more active ingredients and at least one of which comprises a physiologically acceptable blowing agent, and shaping the expanded extrudate to the required active ingredient forms.

6. A process for producing active ingredient forms as claimed in claim 1, which comprises extruding a melt which, besides one or more active ingredients, comprises at least one thermoplastic binder, subjecting the still plastic melt to a shaping, impregnating the solid active ingredient form under pressure with a volatile, physiologically acceptable blowing agent, and subsequently expanding.

7. An active ingredient form obtained by the process as claimed in claim 4.

8. An active ingredient form obtained by the process as claimed in claim 5.

9. An active ingredient form obtained by the process as claimed in claim 6.

* * * * *